(12) United States Patent
Leng et al.

(10) Patent No.: US 11,827,765 B2
(45) Date of Patent: *Nov. 28, 2023

(54) POLYISOPRENE LATEX GRAPHENE COMPOSITES AND METHODS OF MAKING THEM

(71) Applicant: Karex Holdings SDN BHD., Selangor Darul Ehsan (MY)

(72) Inventors: Fook Peng Leng, Johor Darul Takzim (MY); Lai Peng Lim, Johor Darul Takzim (MY); Leng Kian Goh, Johor Darul Takzim (MY); Yi Yee Loh, Johor Darul Takzim (MY); Joon Ching Juan, Kuala Lumpur (MY); Nay Ming Huang, Kuala Lumpur (MY)

(73) Assignee: KAREX HOLDINGS SDN BHD., Selangor Darul Ehsan (MY)

( * ) Notice: Subject to any disclaimer, the term of this patent is extended or adjusted under 35 U.S.C. 154(b) by 47 days.

This patent is subject to a terminal disclaimer.

(21) Appl. No.: 17/539,692

(22) Filed: Dec. 1, 2021

(65) Prior Publication Data

US 2022/0089834 A1    Mar. 24, 2022

Related U.S. Application Data

(63) Continuation of application No. 16/347,015, filed as application No. PCT/MY2017/000039 on Oct. 31, 2017, now Pat. No. 11,214,664.

(30) Foreign Application Priority Data

Nov. 3, 2016 (MY) .............. PI2016001937

(51) Int. Cl.

| | | |
|---|---|---|
| C08K 3/04 | (2006.01) |
| A61B 42/10 | (2016.01) |
| A61B 46/17 | (2016.01) |
| C01B 32/194 | (2017.01) |
| C01B 32/198 | (2017.01) |
| A41D 19/00 | (2006.01) |
| A61F 6/04 | (2006.01) |
| A61L 29/02 | (2006.01) |
| A61L 29/04 | (2006.01) |
| A61L 29/12 | (2006.01) |
| A61L 31/02 | (2006.01) |
| A61L 31/04 | (2006.01) |
| A61L 31/12 | (2006.01) |
| B29C 41/00 | (2006.01) |
| B29C 41/14 | (2006.01) |
| B29C 41/46 | (2006.01) |
| C08J 3/20 | (2006.01) |
| C08J 5/02 | (2006.01) |
| C08K 3/22 | (2006.01) |
| C08K 3/28 | (2006.01) |
| C08K 5/41 | (2006.01) |
| C08K 5/42 | (2006.01) |

(Continued)

(52) U.S. Cl.
CPC .......... *C08K 3/042* (2017.05); *A41D 19/0062* (2013.01); *A61B 42/10* (2016.02); *A61B 46/17* (2016.02); *A61L 29/02* (2013.01); *A61L 29/042* (2013.01); *A61L 29/126* (2013.01); *A61L 31/024* (2013.01); *A61L 31/049* (2013.01); *A61L 31/125* (2013.01); *A61L 31/126* (2013.01); *B29C 41/003* (2013.01); *B29C 41/14* (2013.01); *B29C 41/46* (2013.01); *C01B 32/194* (2017.08); *C01B 32/198* (2017.08); *C07C 333/16* (2013.01); *C08J 3/203* (2013.01); *C08J 5/02* (2013.01); *C08K 3/22* (2013.01); *C08K 3/28* (2013.01); *C08K 5/41* (2013.01); *C08K 5/42* (2013.01); *C08K 5/47* (2013.01); *C08L 7/02* (2013.01); *C08L 9/10* (2013.01); *A61B 42/00* (2016.02); *A61M 25/00* (2013.01); *B29K 2019/00* (2013.01); *B29K 2105/0064* (2013.01); *B29K 2509/02* (2013.01); *C08J 2307/02* (2013.01); *C08K 3/06* (2013.01); *C08K 5/39* (2013.01); *C08K 2003/2296* (2013.01); *C08K 2201/014* (2013.01)

(58) Field of Classification Search
CPC .................... C08K 3/042; C08L 9/00
See application file for complete search history.

(56) References Cited

FOREIGN PATENT DOCUMENTS

| | | |
|---|---|---|
| CN | 102491317 A | 6/2012 |
| CN | 104475076 A | 4/2015 |

(Continued)

OTHER PUBLICATIONS

Nam, Ki-Ho et al., "Sustainable production of reduced graphene oxide using elemental sulfur for multifunctional composites", Composites Part B 176(2019) 107236. (10 Pages total), (Year: 2019).

(Continued)

*Primary Examiner* — Wenwen Cai
(74) *Attorney, Agent, or Firm* — ArentFox Schiff LLP

(57) ABSTRACT

The present invention relates to a method of preparing reduced graphene oxide, incorporation of the reduced graphene oxide into polyisoprene latex to provide a polyisoprene latex graphene composite and elastomeric articles prepared using the polyisoprene latex-graphene composite. In particular, the reduction of graphene oxide is accomplished without the use of strong reducing agents and organic solvents and incorporation of the reduced graphene oxide into polyisoprene latex is accomplished using room temperature latex mixing method or hot maturation. The resultant composite exhibits good colloid stability and polyisoprene latex films produced from the composite exhibit good mechanical properties with improved ageing resistance.

19 Claims, 1 Drawing Sheet

(51) Int. Cl.
*C08L 7/02* (2006.01)
*C08L 9/10* (2006.01)
*C08K 5/47* (2006.01)
*C07C 333/16* (2006.01)
*A61M 25/00* (2006.01)
*B29K 19/00* (2006.01)
*B29K 105/00* (2006.01)
*B29K 509/02* (2006.01)
*C08K 5/39* (2006.01)
*A61B 42/00* (2016.01)
*C08K 3/06* (2006.01)

(56) References Cited

FOREIGN PATENT DOCUMENTS

| | | |
|---|---|---|
| CN | 105037821 A | 11/2015 |
| CN | 105037835 A | 11/2015 |
| CN | 105237828 A | 1/2016 |
| CN | 105694130 A | 6/2016 |
| CN | 105906854 A | 8/2016 |
| CN | 106065095 A | 11/2016 |
| WO | WO 2016/005665 A1 | 1/2016 |

OTHER PUBLICATIONS

Zhong,. B et al., "One-step approach to reduce and modify graphene oxide via vulcanization accelerator and its application for elastorner reinforcement", Chemical Engineering Journal, vol. 317, pp. 51-59, (2017).

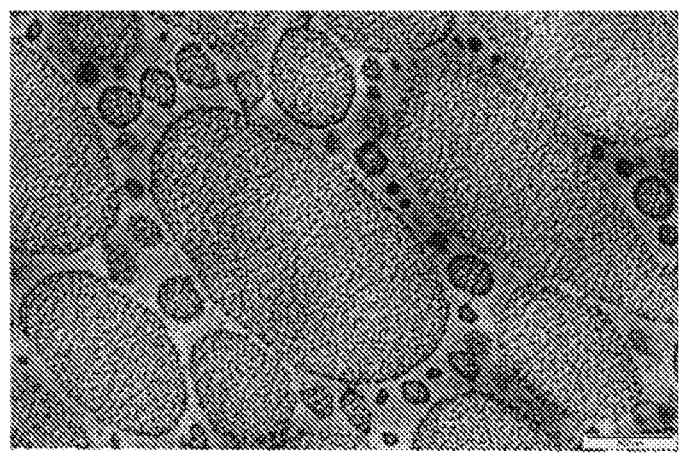
(A)
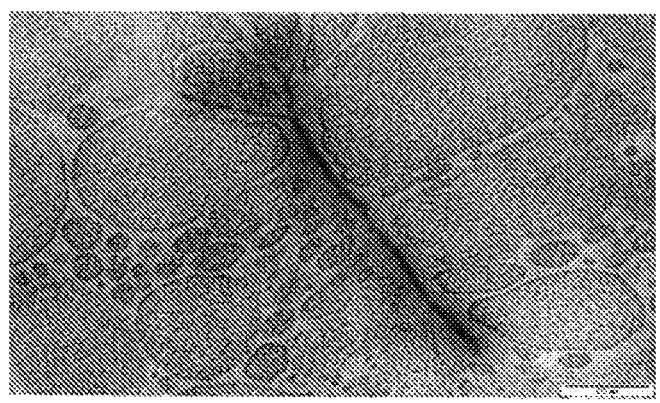
(B)

POLYISOPRENE LATEX GRAPHENE COMPOSITES AND METHODS OF MAKING THEM

CROSS-REFERENCE TO RELATED APPLICATIONS

This application is a continuation of U.S. patent application Ser. No. 16/347,015, filed on May 2, 2019, which is a U.S. National Stage application of PCT International Application No. PCT/MY2017/000039, filed Oct. 31, 2017, which claims priority to Malaysian Patent Application No. PI2016001937, filed Nov. 3, 2016, the disclosures of which are incorporated herein by reference.

FIELD OF THE INVENTION

The present invention relates to a method of preparing reduced graphene oxide, incorporation of the reduced graphene oxide into polyisoprene latex to provide a polyisoprene latex graphene composite and elastomeric articles prepared using the polyisoprene latex graphene composite. In particular, the reduction of graphene oxide is accomplished without the use of strong reducing agents and organic solvents and incorporation of the reduced graphene oxide into polyisoprene latex is accomplished using room temperature latex mixing method or hot maturation. The resultant composite exhibits good colloid stability and polyisoprene latex films produced from the composite exhibit good mechanical properties with improved ageing resistance.

BACKGROUND OF THE INVENTION

Graphene and its derivatives such as graphene oxide, have attracted tremendous attention and research interest since the discovery of graphene in 2004 due to their exceptional thermal, mechanical and barrier properties [Johnson et al., Current Opinion in Colloid & Interface Science, 2015, 20, 367-382]. Polymer nanocomposites (polymer matrix composites with incorporated nanoscale filler materials) are one of the most studied applications for graphene oxide. This could be attributed to the variety of chemical functional groups available and their relatively low cost as compared to pristine graphene. Graphene-polymer nanocomposites show significant mechanical property enhancements at much lower loadings than conventional fillers composite. [Kashyap et al. J. Alloys and Compounds, 2016, 684, 254-260, doi: 10.1016/j.jallcom.2016.05.162].

General approaches or strategies employed to prepare conventional graphene-polymer nanocomposites involve solution mixing, melt blending and in situ polymerisation methods. Performance of graphene-polymer nanocomposites is dependent on the dispersion of graphene in the polymer matrix.

Hence modification of graphene oxide has been widely studied to ensure uniform distribution of graphene oxide in the polymer matrix and at the same time improve the interfacial adhesion between graphene oxide and polymer.

The two common methods used to produce reduced graphene oxide are chemical reduction and thermal reduction. Chemical reduction of graphene oxide is normally achieved through addition of reducing agents, such as hydrazine hydrate, sodium borohydride hydroquinone, citric acid and ascorbic acid, etc. Chemical reduction of graphene oxide usually results in a black precipitation from the original yellow-brown suspension.

Despite various approaches that have been explored, the process to make a homogenous and stable dispersion of graphene oxide in the polyisoprene latex matrix remains a major challenge in this field.

The present inventors have found a method of producing reduced graphene oxide without the use of a strong reducing agent. The inventors have also found a method of achieving homogeneity of the composite dispersion without the use of high shear mixing or ultrasonic mixing. Colloidal stability of the latex was also improved with current invention. Furthermore, elastomeric film produced from the composite exhibits good physical properties and improved resistance to ageing.

SUMMARY OF THE INVENTION

In a first aspect, the present invention provides a polyisoprene latex graphene composite composition comprising:
  i) polyisoprene latex
  ii) at least one stabilizer;
  iii) at least one curing agent; and
  iv) graphene oxide.
  in some embodiments, more than one curing agent is present. In some embodiments, the graphene oxide is reduced graphene oxide.

In another aspect of the invention there is provided a method of preparing reduced graphene oxide comprising:
  a) adjusting the pH of a graphene oxide composition to between about 8 and 12;
  b) adding to the pH adjusted graphene oxide composition one or more curing agents;
  c) mixing the graphene oxide composition by slow agitation at a temperature in the range of from about 20° C. to about 80° C. for a time period in the range of about 4 to about 24 hours.

In some embodiments, more than one curing agent is added to the pH adjusted graphene oxide composition. In some embodiments, one or more stabilizers are added at step a).

In a further aspect of the invention, there is provided a method of preparing a polyisoprene latex graphene composite composition comprising:
  a) preparing a composition of reduced graphene oxide by
    i) adjusting the pH of a graphene oxide composition to in the range of about 8 and 12;
    ii) adding to the pH adjusted graphene oxide composition at least one curing agent;
    iii) mixing the graphene oxide composition by slow agitation at a temperature in the range of from about. 20° C. to about 80 for a period in the range of about 4 to about 24 hours;
  b) preparing a stabilized polyisoprene latex composition by mixing polyisoprene latex with at least one stabilizer under slow agitation for a time period in the range of about 4 to about 24 hours; and
  c) combining the reduced graphene oxide composition of step a) with the stabilized polyisoprene latex composition prepared in step b) and mixing.

In some embodiments, the mixing at step c) is carried out at room temperature. In other embodiments, the mixing at step c) is carried out by slow agitation at a temperature in the range of 40° C. to about 70° C.

In yet another aspect of the present invention, there is provided a method of making an elastomeric article comprising:
  a) preparing a polyisoprene latex. graphene composite composition of the present invention;

b) dipping a former into the polyisoprene latex graphene composite composition to form an elastomeric film on the former; and c) curing the elastomeric film.

In yet a further aspect of the invention, the present invention provides an elastomeric article made by the method of the invention.

In some embodiments, the elastomeric article is a condom, glove, probe cover, finger cot, catheter; tubing or a balloon for a catheter. In a particular embodiment, the elastomeric article is a condom.

BRIEF DESCRIPTION OF THE FIGURES

FIG. 1 provides photographic representations (A) an unfilled, vulcanised (cured) polyisoprene latex film (without graphene oxide) and (B) a latex film of the present invention comprising reduced graphene oxide and prepared using the room temperature latex mixing method.

DETAILED DESCRIPTION OF THE INVENTION

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the pint invention, preferred methods and materials are described.

The articles "a" and "an" are used herein to refer to one or to more than one (i.e. to at least one) of the grammatical object of the article. By way of example, "an element" means one element or more than one element.

As used herein, the term 'about" refers to a quantity, level, value, dimension, size or amount that varies by as much as 30%, 25%, 20%, 15% or 10% to a reference quantity, level, value, dimension, size or amount.

Except where the context requires otherwise due to express language or necessary implication, the word "comprise" or variations such as "comprises" or "comprising" is used in an inclusive sense, i.e. to specify the presence of the stated features but not to preclude: the presence or addition of further features in various embodiments of the invention.

The term "consisting essentially of" or variations such as "consists essentially of" to require the listed components to be present and exclude other components from being present with the exception of that inactive compounds, such as impurities, may be present.

Compositions of the Invention

In a first aspect, the present invention provides a polyisoprene latex graphene composite composition comprising:

i) polyisoprene latex
ii) at least one stabilizer;
iii) at least one curing agent; and
iv) Graphene oxide.

In some embodiments, the polyisoprene latex is natural polyisoprene latex (rubber). In other embodiments, the polyisoprene latex is synthetic polyisoprene latex. Synthetic polyisoprene latex is a synthetic predominantly stereoregular polymer that resembles natural rubber in molecular structure and properties. Polymerisation of isoprene may result in four possible types of repeating units, 1,2-polyisoprene, 3,4-polyisoprene, trans-1,4-polyisoprene and cis-1,4-polyisoprene. In some embodiments, the synthetic polyisoprene latex used has a high proportion of cis-1,4-polyisoprene, such as greater than 85%, more especially greater than 90%, even more especially greater than 95% cis-1,4-polyisoprene. Suitable synthetic polyisoprene latexes include Cariflex® IR0401 and BSTS IRL 701.

In some embodiments, the at least one stabilizer is selected from a metal hydroxide, an anionic surfactant and an anionic dispersant or a. combination thereof. Suitable metal hydroxides include, but are not limited to, potassium hydroxide, sodium hydroxide or aluminium hydroxide. Suitable anionic surfactants include, but are not limited to, alkyl sulfates and alkyl benzene sulfonates and salts thereof, where the alkyl group may be linear or branched, especially $C_8$ to $C_{18}$ sulfates and $C_8$ to $C_{18}$ alkyl benzene sulfonates and salts thereof, more especially $C_{10}$ to $C_{14}$ alkyl sulfates and $C_{10}$ to $C_{14}$ alkyl benzene sulfonates or salts thereof, most especially $C_{12}$ alkyl sulfates and $C_{12}$ alkyl benzene sulfonates and salts thereof, such as sodium dodecyl (lauryl) sulfate (SLS) and sodium dodecyl benzene sulfonate (SDBS). Suitable anionic dispersants include; but are not limited to, sulfonated naphthalene and salts thereof, more especially polymerized alkyl naphthalene sulfonic acids and salts thereof, such. as sodium salt of polymerized alkyl naphthalene sulfonic acids.

In some embodiments, the amount of at least one stabilizer in the composite composition is from about 0.01 phr to about 5.0 phr, especially from about 0.10 phr to about 3.0 phr, more especially from 0.1 phr to 2.0 phr. In particular embodiments, the at least one stabilizer comprises potassium hydroxide in. an amount of from about 0.01 phr to about 0.50 phr. In some embodiments, the at least one stabilizer comprises sodium dodecyl sulfate in an amount of from about 0.50 phr to about 2.0 phr. In some embodiments, the at least one stabilizer comprises sodium salt of polymerized alkyl naphthalene sulfonic acids in an amount of from about 0.10 phr to about 1.0 phr.

In some embodiments, the graphene oxide consists essentially of oxidized graphene sheets. (or 'graphene oxide sheets') having their basal planes decorated with epoxide and hydroxyl groups, in addition to carbonyl and carboxyl groups located at the edges (Lerf-Klinowski model) [Chua and Pumera, Chem. Comm., 2016, 52, 72-75]. The amount of graphene oxide in the composite composition is from about 0.01 to 1.0 phr. Once the graphene oxide comes into contact with the curing agent, at least some of the hydroxyl groups and carboxylic acid groups are reduced to provide a partially reduced graphene oxide.

The curing agent is present to assist. in curing the elastomeric composition when required. However, it is also proposed that the curing agent assists in the reduction of the graphene oxide. In particular embodiments, the at least one curing agent comprises at least one of sulfur, a thiocarbamate such as zinc dibutyl dithiocarbamate (ZDBC) and zinc diethyl dithiocarbamate (ZDEC); a thiuram such as dipentamethylene thiuram tetrasulfide, tetrabenzyl thiuram disulfide, tetraethyl thiamin disulfide, tetramethyl thiuram disulfide, tetrabutyl thiuram disulfide and tetraisobutyl thiuram disulfide; a thiourea such as ethyl thiourea (ETU) and diphenylthiourea (DPTU); thiazoles such as metcapto benzothiazoles (MBT), mercapto benzothiazole disulfide (MBTS) and zinc 2-mercaptobenzothiazole (ZMBT); guanidines such as diphenylguanidine; aldehyde/amine based accelerators such as hexamethylene-tetramine; metal oxides such as lead oxide, magnesium oxide, barium oxide, zinc oxide, manganese oxide, copper oxide, nickel oxide and aluminium oxide, metal hydroxides such as barium hydroxide, manganese. hydroxide, copper hydroxide, nickel hydroxide, aluminium hydroxide; or mixtures thereof. In particular embodiments, the at least one curing agent comprises at least one curing agent selected from sulfur, a dithiocarbomate, a thiazole and a metal oxide. In some embodiments, the at least one curing agent is a combination of sulfur, a dithiocarbamate, a thiazole and a metal oxide. In some embodiments, the at least one curing agent consists essentially of a combination of sulfur, zinc diethyldithiocarbamate, zinc dibutyldithiocarbamate, zinc 2-mercaptobenzothiazole and zinc oxide.

In some embodiments, the amount of at least one curing agent in the composite composition is from about 0.50 phr to about 8.0 phr, especially from about 0.50 phr to about 5.50 phr. In particular embodiments, the at least one curing agent comprises sulfur in an amount of from about 0.3 phr to about 1.5 phr. In some embodiments, the at least one curing agent comprises dithiocarbamates in an amount of from about 0.1 phr to about 2.0 phr. In some embodiments, the at least one curing agent comprises a thiazole in an amount of from about 0.01 phr to about 1.0 phr. In some embodiments, the at least one curing agent comprises a metal oxide in an amount of from about 0.1 phr to about 1.0 phr.

The composition of the invention may also include additional optional components such as pH adjusters, antioxidants, antiozonants and solvents.

The pH adjuster is used to maintain the graphene oxide and. composite composition at the required pH. The pH of the composite composition is suitably adjusted to be in the range of about 8.5 to about 13.5, especially in the range of about 9 to about 12.0. Exemplary pH adjusters include potassium hydroxide, sodium hydroxide and/or ammonium hydroxide, especially ammonium hydroxide. The amount of pH adjuster can range from about 0.1 to 3.0 phr, 0.1 to 2.5 phr, 0.1 to 2.0 phr, 0.1 to 1.5 phr, 0.1 to 1.0 phr, 0.1 to 0.5 phr, 0.1 to 0.3 phr, 0.2 to 3.0 phr, 0.2 to 2.5 phr, 0.2 to 2.0 phr, 0.2 to 1.5 phr, 0.2 to 1.0 phr, 0.2 to 0.5 phr, 0.2 to 0.3 phr, 0.5 to 3.0 phr, 0.5 to 2.5 phr, 0.5 to 2.0 phr, 0.5 to 1.5 phr or 0.5 to 1.0 phr.

An antioxidant may be added to the composite composition of the present invention. Suitable antioxidants include hindered arylamines or polymeric hindered phenols, and Wingstay L or Ralox LC (the product of reaction of p-cresol and dicyclopentadiene). The antioxidant may, for example, be added in an amount ranging from about 0.1 to about 3.0 phr, such as about 0.1 to about 2.0 phr, about 0.5 to about 1.5 phr or about 0.5 to about 1.0 phr.

Antiozonants may be used in the elastomeric composite composition. Suitable anitozonants include paraffinic waxes, microcrystalline waxes and intermediate types (which are blends of both paraffinic and microcrystalline waxes). The amount of antiozonant may range from about 0.1 to about 5.0 phr, 0.1 to about 3.0 phr, about 0.1 to about 1.5 phr, about 0.5 to about 5.0 phr, about 0.5 to about 3.0 phr, or about 0.5 to about 1.5 phr.

The elastomeric composition may also comprise a solvent. In some embodiments, the solvent is an aqueous solvent such as water or ammoniated water. In some embodiments, the water content is 30 to 65%, especially 35 to 55%, more especially 40 to 45% w/w of the composition. In particular embodiments, the pH of the composition is in the range of 9 to 13, especially 10 to 12.

The total solids content of the composition is in the range of 30 to 80%, especially 40 to 50% or 50 to 65%. In some embodiments, the total solids content is in the range of 40 to 55%.

Methods of Preparing Reduced Graphene Oxide

In another aspect of the invention there is provided a method of preparing reduced graphene oxide comprising:
a) adjusting the pH of a graphene oxide composition to between about 8 and 12;
b) adding to the pH adjusted graphene oxide composition at least one curing agent;
c) mixing the graphene oxide composition by slow agitation at a temperature in the range of from about 20° C. to about 80° C. for a period in the range of about 4 to about 24 hours.

The pH adjuster is used to maintain the graphene oxide composition at the required pH. The pH of the graphene oxide composition is suitably adjusted to be in the range of about 8.0 to about 12.0, especially in the range of about 9 to about 12.0. Exemplary pH adjusters include potassium hydroxide, sodium hydroxide and/or ammonium hydroxide, especially ammonium. hydroxide. The amount of pH adjuster can range from about 0.1 to 3.0 phr, 0.1 to 2.5 phr, 0.1 to 2.0 phr, 0.1 to 1.5. phr, 0.1 to 1.0 phr, 0.1 to 0.5 phr, 0.1 to 0.3 phr, 0.2 to 3.0 phr, 0.2 to 2.5 phr, 0.2 to 2.0 phr, 0.2 to 1.5 phr, 0.2 to 1.0 phr, 0.2 to 0.5 phr, 0.2 to 0.3 phr, 0.5 to 3.0 phr, 0.5 to 2.5 phr, 0.5 to 2.0 phr, 0.5 to 1.5 phr or 0.5 to 1.0 phr.

In particular embodiments, the at least one curing agent comprises at least one of sulfur, a thiocarbamate such as zinc dibutyl dithiocarbamate (ZDBC) and zinc diethyl dithiocarbamate (ZDEC); a thiuram such as dipentamethylene thiuram tetrasulfide, tetrabenzyl thiuram disulfide, tetraethyl thiuram disulfide, tetramethyl thiuram disulfide, tetrabutyl thiuram disulfide and tetraisobutyl thiuram disulfide; a thiourea such as ethyl thiourea (ETU) and diphenylthiourea (DPTU); thiazoles such as metcapto benzothiazoles (MBT), mercapto benzothiazole disulfide (MBTS) and zinc 2-mercaptobenzothiazole (ZMBT); guanidines such as diphenylguanidine; aldehyde/amine based accelerators such as hexamethylene-tetramine; metal oxides such as lead oxide, magnesium oxide, barium oxide, zinc oxide, manganese oxide, copper oxide, nickel oxide and aluminium oxide, metal hydroxides such as barium hydroxide, manganese hydroxide, copper hydroxide, nickel hydroxide, aluminium hydroxide; or mixtures thereof. In particular embodiments, the at least one curing agent comprises at least one curing agent selected from sulfur, a dithiocarbamate, a thiazole and a metal oxide. In some embodiments, the at least one curing agent is a combination of sulfur, a dithiocarbamate, a thiazole and a metal oxide. In some embodiments, the at least one curing agent consists essentially of a combination of sulfur, zinc diethyldithiocarbamate, zinc dibutyldithiocarbamate, zinc 2-mercaptobenzothiazole and zinc oxide.

In some embodiments, the amount of at least one curing agent in the composite composition is from about 0.50 phr to about 8.0 phr, especially from about 0.50 phr to about 5.50 phr. In particular embodiments, the at least one curing agent comprises sulfur in an amount of from about 0.3 phr to about 1.5 phr. In some embodiments, the at least one curing agent comprise dithiocarbamates in an amount of from about 0.1 phr to about 2.0 phr. In some embodiments, the at least one curing agent comprises a thiazole in an amount of from about 0.01 phr to about 1.0 phr. In some embodiments, the at least one curing agent comprises a metal oxide in an amount of from about 0.1 phr to about 1.0 phr.

In some embodiments, at least one stabilizer is added at step a). In some embodiments, the at least one stabilizing agent is an anionic dispersant. In particular embodiments, the anionic dispersant is selected from a sulfonated naphthalene and salts thereof, more especially polymerized alkyl naphthalene sulfonic acids and salts thereof, such as sodium salt of polymerized alkyl naphthalene sulfonic acids.

The at least one stabilizer is present in an amount in the range of 0.1 phr to 2.0 phr. In some embodiments, the at least one stabilizer comprises sodium salt of polymerized alkyl naphthalene sulfonic acids in an amount of from about 0.10 phr to about 1.0 phr.

The reducing effect of the curing agents on. the graphene oxide increases with temperature and with time agitated. As the temperature of the reaction is increased, the reducing effect is increased. Furthermore, the longer the reaction is agitated, the more reducing effect is observed. As the reaction progresses, the mixture changes from a brown colour to a black colour. The temperature of the reaction mixture and the time agitated for may be adjusted to provide the desired extent of reduction of the graphene oxide. In particular embodiments, the graphene oxide is partially reduced. In some embodiments, the reaction mixture is agitated for a period of time in the range of 10 to 24 hours, especially 15 to 24 hours. In some embodiments, the mixture is agitated at a temperature of 20° C. to 80° C., especially 30° C. to 50° C.

Methods of Preparing a Polyisoprene Latex Graphene Composite Composition

In one aspect of the invention, there is provided a method of preparing a polyisoprene latex graphene composite composition comprising:
  a) Preparing a composition of reduced graphene oxide by
    i) adjusting the pH of a graphene oxide composition to in the range of about 8 and 12;
    ii) adding to the pH adjusted graphene oxide composition at least one curing agent;
    iii) mixing the graphene oxide composition by slow agitation at a temperature in the range of from about 20° C. to about 80° C. for a period in the range of about 4 to about 24 hours;
  b) preparing a stabilized polyisoprene latex composition by mixing a polyisoprene latex with at least one stabilizer under slow agitation for a time period in the range of about 4 to about 24 hours; and
  c) combining the reduced graphene oxide composition of step a) with the stabilized polyisoprene latex composition prepared in step b) and mixing.

In some embodiments, the reduced graphene oxide composition is prepared as described above.

In some embodiments, the pre-stabilized polyisoprene latex is stabilized by at least one stabilizer selected from a metal hydroxide, an anionic surfactant and an anionic dispersant or a combination thereof, especially a metal hydroxide and/or a anionic surfactant. Suitable metal hydroxides include, but are not limited to, potassium hydroxide, sodium hydroxide or aluminium hydroxide. Suitable anionic surfactants include, but are not limited to, alkyl sulfates and alkyl benzene sulfonates and salts thereof, where the alkyl group may be linear or branched, especially $C_8$ to $C_{18}$ alkyl sulfates and $C_8$ to $C_{18}$ alkyl benzene sulfonates and salts thereof, more especially $C_{10}$ to $C_{14}$ alkyl sulfates and $C_{10}$ to $C_{14}$ alkyl benzene sulfonates or salts thereof most especially $C_{12}$ alkyl sulfates and $C_{12}$ alkyl benzene sulfonates and salts thereof, such as sodium dodecyl (lauryl) sulfate (SLS) and sodium dodecyl benzene sulfonate (SDBS). In some embodiments, the stabilizer is a combination of metal hydroxide and anionic surfactants, especially a combination of potassium hydroxide and sodium dodecyl sulfate.

In some embodiments, the amount of at least one stabilizer in the stabilized polyisoprene latex composition is from about 0.01 phr to about 5.0 phr, especially from about 0.10 phr to about 3.0 phr, more especially from 0.1 phr to 2.0 phr. In particular embodiments, the at least one stabilizer comprises potassium hydroxide in an amount of from about 0.01 phr to about 0.50 phr. In some embodiments, the at least one stabilizer comprises sodium dodecyl sulfate in an amount of from about 0.50 phr to about 2.0 phr.

In step c) the reduced graphene oxide composition and the stabilized polyisoprene latex composition are combined. The reduced graphene oxide composition may be added to the polyisoprene latex composition or the polyisoprene latex composition may be added to the reduced graphene oxide composition. In general, the reduced graphene latex composition is a smaller volume and is therefore conveniently added to the polyisoprene latex composition.

In some embodiments, the mixing at step c) is carried out at room temperature (room temperature latex mixing). In other embodiments, the mixing at step c) is carried out by slow agitation at a temperature in the range of 40° C. to about 70° C., especially 40° C. to 60° C., (hot maturation) for a period of about 8 to about 24 hours especially about 12 to 16 hours.

In step c), the polyisoprene-latex composition is slow agitated until the components have been mixed uniformly or to homogeneity. In some embodiments, this reclaims 8 to 24 hours of slow agitation.

After mixing at room temperature, the composition is allowed to mature at room temperature until it has reached a µm-cure of 80-100% swell in toluene. Generally, maturation occurs over a period of from about 1 to 15 days, especially from about 5 to 10 days, As maturation occurs, the % toluene swell drops, indicating at least some cross-linking of the polyisoprene latex has taken place.

After use of the hot maturation process of slow agitation at 40° C. to about 70° C., especially 40° C. to 60° C., for a period of about 8 to about 24 hours, especially about 12 to 16 hours, the composite composition will have attained a pre-cure of 80-100% swell in toluene and will be ready to use.

In general, colloidal stability of the polyisoprene latex tends to decrease with increasing age of latex. Destabilization of colloidal latex is normally indicated by increasing viscosity and decreasing mechanical stability after compounding incompatibility between reduced graphene oxide. and polymer matrixes could further aggravate the stability of the latex. In the present invention, colloidal stability of the composite significantly improved even with the use of older age latex.

The reduced graphene oxide showed good compatibility with polyisoprene latex as homogeneous dispersion of graphene in the latex film is observed. FIG. 1 shows network visualization of the latex film cast from the composites. Distortion of the latex particles adjacent to the reduced graphene oxide is observed, this indicates that the reduced graphene oxide particles are connected to or crosslinked with the latex particles.

Preparation. of the composite composition is accomplished by using a normal latex. mixing method without the need of ultrasonication or high shear mixing. Furthermore, the reduced graphene oxide is prepared without the need of strong reducing agent or organic solvent.

Elastomeric Articles and Methods for Making them

In yet another aspect of the present invention, there is provided a method of making an elastomeric article comprising:
  a) preparing a polyisoprene latex graphene composite composition as described above;

b) dipping a former into the polyisoprene latex graphene composite composition to form an elastomeric film on the former; and c) curing the elastomeric film.

In yet another aspect; there is provided an elastomeric article prepared by the above method.

The elastomeric article may be prepared using conventional equipment.

In particular embodiments, the elastomeric article is selected from a condom, a glove, a probe cover, fingercots, catheters, tubing, balloons for catheters and the like. In particular embodiments the elastomeric article is a condom.

The former suitable to make the elastomeric article of choice is dipped into the elastomeric composition described above.

In some embodiments, the former, typically glass or ceramic, is cleaned and dried prior to dipping in the elastomeric composition. Cleaning is an important process to avoid imperfections such as pinholes in the elastomeric articles. Cleaning may be performed in alkaline solution, for example, with solutions of ammonia, sodium carbonate (soda ash) or sodium hydroxide. After washing with alkaline solution, the former is rinsed clean with water and dried. The former may be dried by brushing, with an air curtain or with hot air. The former is then allowed to come to room temperature before the dipping step is performed.

The former is dipped in the polyisoprene latex graphene composite composition for an amount of time to ensure the former is evenly coated, but not so long as to develop a thicker than necessary coating. The time in which the former is in the elastomeric composition depends on the desired thickness of the polyisoprene latex graphene composite film. Typical times in which the former is held in the elastomeric composition include from about 1 to about 60 seconds, for example, between about 1 and about 50 seconds, about 1 to about 40 seconds or about 1 to about 30 seconds. In particular embodiments, the dipping process is a continuous process. In some embodiments, the time between immersion and withdrawal of the former from the polyisoprene latex graphene composite composition is about 1 to 5 seconds.

In some embodiments, the elastomeric composition is maintained at a temperature between 20° C. and 30° C. during the dipping step.

In some embodiments, the polyisoprene latex graphene composite composition is constantly mixed to ensure good homogeneity of the composition during the dipping process.

The polyisoprene latex graphene composite coating on the dipped former is then allowed to at least partially dry. The drying step may be carried out at room temperature or may be carried out at elevated temperature for a time sufficient to at least partially dry the polyisoprene latex graphene composite coating. In particular embodiments, the polyisoprene latex graphene composite coating is fully dried. For example, in a particular embodiment, the polyisoprene latex graphene composite coating on the former is dried at about 40° C. to about 100° C. for about 1 to about 10 minutes, especially about 50° C. to about 90° C. for about 1 to about 8 minutes or about 60° C. to about 90° C. for about 1 to about 7 minutes or about 70° C. to about 90° C. for about 1 to about 5 minutes.

Optionally the steps of dipping the former into an polyisoprene latex graphene composite composition and at least partially drying the polyisoprene latex graphene composite coating are repeated one or more times to provide two or more coats of elastomeric composition on the first coating of polyisoprene latex graphene composite composition. In some embodiments, in the first dipping step and the second dipping step and any subsequent dipping step, the elastomeric composition into which the former is dipped is the same polyisoprene latex graphene composite composition. In some embodiments, the second. drying step is performed at a temperature and fora time sufficient to at least partially dry the second polyisoprene latex graphene composite coating. In some embodiments, the second drying step is the same as the first drying step. In other embodiments, the second drying step is different from the first drying step. For example, the second drying step may occur at a temperature lower than the first drying step where the polyisoprene latex graphene composite coating on the former is dried at about 30° C. to about 90° C. for about 1 to about 10 minutes, especially about 40° C. to about 80° C. for about 1 to about 8 minutes or about 50° C. to about 80° C. for 2 to 6 minutes. In some embodiments, only one dipping and drying step is used to form the elastomeric article. In other embodiments, more than one dipping and drying step are used to form the elastomeric article.

The former and dried polyisoprene latex graphene composite coating may be used directly in the next step or may be cooled to room temperature. The former and polyisoprene latex graphene composite coating may be cooled to a desired temperature if a further dipping step is performed. The former and polyisoprene latex graphene composite coating may be used directly in the curing step if no further dipping step is performed.

Once the desired number of layers of polyisoprene latex graphene composite coating has been achieved, the polyisoprene latex graphene composite coating is cured to form the elastomeric article. The curing step may be performed in an oven at a temperature between about 60° C. and about 120° C., especially at a temperature of about 60° C. to about 110° C., about 60° C. to about 100° C. or about 60° C. to about 90° C. The curing may be performed: for a time that provides effective crosslinking between synthetic polyisoprene particles in the polyisoprene latex graphene composite coating and in some embodiments crosslinking between the graphene oxide particles and the polyisoprene latex particles. For example, curing may occur over about 10 to about 60 minutes, especially about 10 to about 50 minutes, more especially about 1.0 to about 40 minutes, more especially about 10 to about 30 minutes. In some embodiments, the curing step is performed using hot air. In other embodiments, the curing step is performed using infrared radiation.

The elastomeric article can be subjected to one or more further process steps prior to stripping of the film or article from the former. These optional steps include cooling, chlorination, post-curing rinsing, polymer coating, powder coating and additional drying steps. The use of these steps may depend on the elastomeric article being produced.

A post-curing, rinse and leaching step may be performed to remove extractable components, for example, unwanted or unreacted components such as surfactants and salts. In some embodiments, the elastomeric article on the former is soaked in water to leach any soluble components. In other embodiments, the elastomeric article on the former is soaked in ammoniated water, weak potassium hydroxide or weak sodium hydroxide solutions, for example, potassium or sodium hydroxide solutions that are about 0.5 to 1.5%. The rinsing or leaching solution may be carried out at ambient temperature or at elevated temperature. For example the rinsing or leaching solution may be at a temperature between ambient temperature and about 80° C.; such as about 40° C. to about 80° C., about 50° C. to about 80° C. or about 55° C. to about 75° C. The elastomeric film and former may be dipped in the rinsing or leaching solution for a time sufficient to remove the desired amount of soluble components. For example, a suitable time is about 1 to about 30 minutes, especially about 1 to about 20 minutes, more especially about 1 to about 10 minutes, most especially about 1 to about 5 minutes.

The elastomeric article may be stripped from the former using known techniques. For example, the elastomeric article may be stripped by the former using an alkaline water and/or powder slurry and/or brushing. The powder slurry contains silica and/or calcium carbonate and has an alkaline pH in the range of about 8.0 to 10.0.

Once the elastomeric article is stripped from the former, it is washed before being dried. Suitably, the elastomeric article is washed with a slurry comprising silica and/or magnesium carbonate and/or calcium carbonate and/or modified cornstarch and/or with a silicone emulsion. Suitable slurries are commercially available. A suitable drying step would be to tumble dry the elastomeric articles at a suitable temperature for a suitable time. Typically, the elastomeric articles are tumble dried at a temperature between about 90° C. and about 110° C. for a time between about 30 to about 60 minutes.

Additional steps may be included in the method of making the elastomeric article as required and as known in the art. For example, in the manufacture of some elastomeric articles, such as gloves and catheters, the former may be initially dipped in a coagulant solution. In the manufacture of condoms, after the dipping steps are complete and before the curing step, a ring may be formed on the condom and after curing, the condom may be electronically tested for pinholes, lubricated, rolled and packaged in foil. Gloves may be subjected to beading/cuffing to create a bead or cuff at the wrist edge of the glove.

In the case of condoms, in particular embodiments, after the condom is removed from the former and dried, it is subjected to electronic testing on a high voltage pin-hole machine as known in the art. For example, the condom is put on an aluminium mandrel manually and the mandrel is rotated against a counter rotating conductive rubber brush. A high voltage current is then applied via the conductive brush. As the condom is made of rubber latex, which has an insulative property, any pin-hole present on the surface will trigger the test machine to remove it automatically to the reject bin. The remaining condoms are then rolled up and collected for foiling.

Foiling of condoms is done by methods known in the art. For example, the rolled condoms are placed on a feeding belt, transported and automatically squeezed into the cells of sealing cylinders. The condoms are pre-lubricated with lubricant such as optionally flavored silicone fluid while on the feeding belt of the foiling machine. During the placement in the sealing cylinders, the condom has direct contact with the foil, which is a heat-sealable film, taken from two reels and surrounding the condom. The edges of the film are then hermetically sealed.

In some embodiments, particularly those where the elastomeric article is a glove or catheter, the optional step of dipping the former into a coagulant solution is performed before the former is dipped in the elastomeric composition. The clean former is dipped into a coagulant solution to provide a thin coating of coagulant on the former. In some embodiments, the coagulant is a salt solution containing ions. In this embodiment, dipping the former into the coagulant leaves a thin coating of the charged ions on the surface of the former. The charged ion coating can assist in controlling the amount elastomeric composition that will subsequently remain on the surface of the former after dipping into the composition, through charge interactions.

The coagulant composition may include ions that are cationic or anionic. Generally metal ion solutions containing cations are suited to a broad range of elastomeric polymers. Examples of such metal salt ions are sodium, calcium, magnesium, barium, zinc, and aluminium. The counter ions may be halides (such as chloride), nitrate, acetate or sulfate, amongst others. In the case of calcium ion-containing coagulants, the calcium ions can be provided as a solution of calcium nitrate or calcium chloride.

The coagulant may also include any other agents, such as wetting agents (such as fatty alcohol ethoxide or other suitable surfactants), anti-tack agents, anti-foaming agents and/or mould release agents, such as. silicon emulsions, polymer release agents and metallic stearates, examples of which are zinc, calcium and potassium stearates.

The concentration of ions in the coagulant can broadly be in the range of 0.0-50% by weight of the coagulant solution (measured as the compound of the multivalent ion in the solution of the multivalent ions), depending on the desired thickness of the elastomeric film layers and the number of layers to be applied (i.e. one layer or two or more layers). In the case of thinner layers, the concentration is suitably in the range of 0.0-20%, 0.0-1.5%, 0.0-1.2%, 1.5-20%, 1.5-15%, 1.0-10%, 1.5-10%, 4-10%, 5-10%, 5-35%, 10-30%, 7-40%, 8-50% and 5-45%. Preferably, the concentration is in the range of 10-30%.

The coagulant may also include metallic stearates in a concentration in the range of about 0.1-5.0% by weight, suitable wetting agents in a concentration in the range of about 0.001-1.0%, and/or antifoaming agents in a concentration in the range of 0.001-1.0% by weight.

The former may be dipped into the coagulant composition for a period of about 1 to about 30 seconds, for example, about 5 to about 20 seconds, about 5 to about 15 seconds or about 1 to 10 seconds.

The elastomeric article may be made from one layer or multiple layers of the composite.

The thickness of the final elastomeric film will depend on the number of layers of polyisoprene latex graphene composite composition used it make the elastomeric article. The thickness of the final film can be in the range of 0.01-3 mm, for example, 0.01-3.0 mm, such as 0.01-2.5 mm, 0.01-2.0 mm, 0.01-1.5 mm, 0.01-1.0 mm, 0.01-0.5 mm, 0.01-0.4 mm, 0.01-0.3 mm, 0.01-0.2 mm, 0.02-0.2 mm, 0.01-0.10 mm, 0.03-3.0 mm, 0.03-2.5 mm, 0.03-2.0 mm, 0.03-1.5 mm, 0.03-1.0 mm, 0.03.0.5 mm, 0.03-0.4 mm, 0.03-0.3 mm, 0.03-0.2 mm, 0.03-0.10 mm, 0.05-3.0 mm, 0.05-2.5 mm, 0.05-2.0 mm, 0.05-1.5 mm, 0.05.1.0 mm, 0.05-0.5 mm, 0.05-0.4 mm, 0.05-0.3 mm, 0.05-0.2 mm, 0.05-0.10 mm, 0.08-3.0 mm, 0.08-2.5 mm, 0.08-2.0 mm, 0.08-1.5 mm, 0.08-1.0 mm, 0.08-0.5 mm, 0.08-0.4 mm, 0.08-0.3 mm, 0.08-0.2 mm, 0.08-0.10 mm, 0.1-3.0 mm, 0.1-2.5 mm, 0.1-2.0 mm, 0.1-1.5 mm, 0.1-1.0 mm, 0.1-0.5 mm, 0.1-0.4 mm, 0.1-0.3 mm, 0.1-0.2 mm, 0.15-3.0 mm, 0.15-2.5 mm, 0.15-2.0 mm, 0.15-1.5 mm, 0.15-1.0 mm, 0.15-0.5 mm, 0.15-0.4 mm, 0.15-0.3 mm, 0.15-0.2 mm, 0.02-0.08 mm, 0.03-0.08 mm, or 0.05-0.08 mm. In particular embodiments, the elastomeric article has a thickness of 0.05 to 0.10 mm.

The elastomeric articles of the present invention have good or enhanced mechanical properties.

In some embodiments, the elastomeric articles of the invention have a higher tensile strength, a higher modulus at 300%, 500% and 700%, similar elongation to break when compared to elastomeric articles produced from unfilled, vulcanized (cured) polyisoprene latex. The tensile strength, modulus at 300%, modulus at 500%, modulus at 700% and elongation to break can be measured using standard methods known in the art such as ASTM Test Method D412-06a (2013).

The elastomeric articles of the present invention also have good ageing resistance. This was tested by accelerated aging procedures to determine whether the elastomeric articles would deteriorate upon storage. In the present case, elastomeric articles made by the methods of the present invention were subject to heat aging for 22 hours at 100° C. The heat aged samples were tested for tensile strength, modulus at 300%, modulus at 500%, modulus at 700% and elongation to break and found to have better physical properties and retention as compared to unfilled, vulcanized polyisoprene latex and composite prepared using normal mixing method.

Without wishing to be bound by theory, it is believed that the improved mechanical properties could be attributed to the bonding/connection/crosslinking between the rubber (polyisoprene latex) particles and reduced graphene oxide.

In order that the invention be readily understood and put into practical effect, particular embodiments will now be described by way of the following non-limiting examples.

EXAMPLES

Example 1 a) polyisoprene latex graphene composite graphene composite having the components set forth in Table 1 was formulated as follows. All components set forth in Table 1 are reported as parts per hundred rubber (phr).
b) The pH of the graphene oxide of Part 13 of Table 1 was adjusted to about 10 using a 0.5% ammonium hydroxide solution. The pH adjusted graphene oxide was then mixed with the other components listed in Part C of Table 1 under slow agitation at 30-35° C. for 16 hours. During this time, the composition changed colour from light brown to dark brown/black.
c) The polyisoprene latex composition was prepared by mixing the components of Part A in Table 1 for 12 to 16 hours at room temperature.
d) The polyisoprene graphene composite was prepared by adding the reduced. graphene composition prepared in b) above to the polyisoprene latex composition of c) above and stirring slowly at room temperature (Method 1).

TABLE 1

| Rubber graphene composite compositions | |
| --- | --- |
| Ingredients | phr |
| Part A | |
| Polyisoprene latex | 100 |
| KOH | 0.01-0.50 |
| Sodium Dodecyl Sulfate | 0.5-2.0 |
| Part B | |
| Graphene Oxide | 0.01-1.0 |
| Sodium Salt of Polymerized Alkyl Naphthalene Sulfonic Acids | 0.10-1.00 |
| Ammonium Hydroxide Solution | To adjust pH from about 9.0 to about 12.0 |
| Part C | |
| Sulphur | 0.30-1.50 |
| Zinc Diethyldithiocarbamate | 0.1-1.0 |
| Zinc Dibutyldithiocarbamate | 0.01-1.0 |

TABLE 1-continued

| Rubber graphene composite compositions | |
| --- | --- |
| Ingredients | phr |
| Zinc 2-mercaptobenzothiazole | 0.01-1.0 |
| Zinc Oxide | 0.1-1.0 |
| Ralox LC or Wingstay L | 0.5-1.5 | e) The composite prepared by using room temperate m mixing preparation methods, with about 80 to about 100% swell in toluene were used to produce latex films with thickness between 0.050-0.070 mm. tin unfilled, vulcanised polyisoprene latex film was prepared using the components of parts A and C of 'fable L The films were prepared by dipping a former into the composite. The former was dipped into the composite twice with about 2 to 3 second dwell time in the composite. The first layer of the dip film was partially dried at about 70° C. for 1-2 minute before the second dip occurred. Each of the films was then cured at about 100° C. for 15 minutes. The tensile strength, 300% modulus, 500% modulus, 700% modulus and elongation of each cured film were tested in accordance with ATM Test Method D412-06a (2013) "Standard Test Methods for Vulcanized Rubber and Thermoplastic Elastomers—Tension". The results are set forth in Table 2.

TABLE 2

Physical properties of latex films prepared using composite compositions

| | Curing temperature, 100° C. for 15 minutes | | |
| --- | --- | --- | --- |
| Properties | Unfilled, Vulcanised latex | Method 1 | Method 2 (Hot maturation) |
| Unaged | | | |
| M300, MPa | 1.75 | 2.00 | 1.89 |
| M500, MPa | 4.05 | 5.14 | 5.22 |
| M700, MPa | 18.65 | 21.57 | 22.113 |
| Tensile, MPa | 35.42 | 37.57 | 29.45 |
| Elongation at break, % | 815 | 815 | 795 |
| Aged 100° C. for 22 hours | | | |
| M300, MPa | 1.45 | 1.86 | 1.65 |
| M500, MPa | 2.63 | 3.73 | 3.60 |
| M700, MPa | 9.80 | 15.78 | 14.46 |
| Tensile, MPa | 32.23 | 35.63 | 27.98 |
| Elongation at break, % | 907.5 | 842.5 | 830 |
| % Retention | | | |
| M300, MPa | 83 | 93 | 87 |
| M500, MPa | 65 | 73 | 69 |
| M700, MPa | 53 | 73 | 65 |
| Tensile, MPa | 91 | 95 | 95 |
| Elongation at break, % | 111 | 103 | 104 | f) The initial physical properties i.e. tensile strength, 300% modulus, 500% modulus, 700% modulus and elongation of the elastomeric articles from the present invention is higher compared to unfilled, vulcanized latex films. About 6% to about 27% increase on various properties observed for Method 1.
g) The latex films also subjected to accelerated ageing at 100° C. for 22 hours. The heat-aged samples were tested for tensile strength, 300% modulus, 500% modulus, 700% modulus and elongation applying ASTM Test Method D412-06a (2013). Percentage retention on the physical properties of the composite is higher as compared to unfilled, vulcanized latex film. Percentage of retention for tensile strength, 300% modulus, 500% modulus and 700% modulus increased by 4%, 10%, 8% and 20% respectively for Method 1.

Example 2 a) Polyisoprene latex graphene composite having the components set forth in Table 1 was formulated as follows. All components set forth in Table 1 are reported as parts per hundred rubber (phr).
b) The polyisoprene latex composition was prepared by mixing the components of Part A in Table 1 for 12 to 16 hours at room temperature.
c) The pH of the graphene oxide of Part B of Table 1 was adjusted to about 12 using a 25% ammonium hydroxide solution.
d) The pH adjusted graphene oxide was then mixed with the other components listed in Part C of Table 1 under slow agitation at 35° C. for 16 hours. During this time, the composition changed colour from light brown to dark brown/black.
e) The polyisoprene graphene composite was prepared by adding the reduced graphene composition prepared in d) above to the polyisoprene latex composition of b) above and stirring slowly at 45-50 (Method 2).

The composite prepared by hot maturation attained. about. 80 to about 90% swell after 16 hours of maturation. The composite latex were used to produce latex films with thickness between 0.050-0.070 mm. The films were prepared and tested using the same methods as c) in Example 1. The results are set forth in Table 2 above.

Example 3

Colloidal properties of the composite formulated by methods known in the art is as shown in Table 3.

TABLE 3

Colloidal properties of the latex composite.

| Properties | Unfilled, Vulcanised, latex | Post addition of unreduced graphene oxide | Method 1 | Method 2 |
|---|---|---|---|---|
| Total Solids Content, % | 45.13 | 45.20 | 45.32 | 45.07 |
| BF viscosity, sp1/60 rpm, cps | 146 | 182.5 | 55 | 17.5 |

Viscosity of the composite compositions compounded using about 3 month old latex is summarized in Table 3. Based on the results, viscosity of the composite prepared by the methods of the invention showed the lowest value. This indicates that the composite prepared by the method of invention is stable.

What is claimed is:

1. A method of preparing an elastomeric article comprising:
    a) dipping a former into a polyisopropene latex graphene composite composition comprising polyisoprene latex bonded to or cross-linked with an at least partially reduced graphene oxide and at least one stabilizer, to form an elastomeric film on the former; and
    b) curing the elastomeric film to provide an elastomeric article, wherein the former is optionally dipped into a coagulant solution before step a).

2. The method of claim 1, wherein the method comprising dipping a former into a coagulant solution before step a).

3. The method of claim 1, wherein the coagulant solution comprises metal salt ions of sodium, calcium, magnesium, barium, zinc or aluminum.

4. The method of claim 1, wherein the coagulant solution comprises a metallic stearate in a concentration of about 0.1 to 5.0% by weight, a wetting agent in a concentration of about 0.001 to 1.0% by weight and/or an anti-foaming agent in a concentration of 0.001 to 1.0% by weight.

5. The method of claim 1, wherein the at least one stabilizer is selected from the group consisting of: a metal hydroxide, an anionic surfactant, an anionic dispersant, and a combination thereof.

6. The method of claim 1, wherein the at least one stabilizer is selected from the group consisting of: potassium hydroxide, sodium dodecyl sulfate, sodium salt of polymerized alkyl naphthalene sulfonic acid, and mixtures thereof.

7. The method of claim 1, wherein the at least one stabilizer is present in an amount of from about 0.01 phr to 5.0 phr.

8. The method of claim 1, wherein the polyisopropene latex graphene composite composition further comprises an antioxidant.

9. The method of claim 8, wherein the antioxidant is a hindered arylamine or a polymeric hindered phenol or a reaction product of p-cresol and dicyclopentadiene.

10. The method of claim 8, wherein the antioxidant is present in an amount of from 0.1 to 3.0 phr.

11. The method of claim 1, wherein the polyisopropene latex graphene composite composition further comprises a pH adjuster.

12. The method of claim 1, wherein the polyisoprene latex graphene composite composition has a pH from 8.5 to 13.5.

13. The method of claim 1, wherein the at least partially reduced graphene oxide is in an amount of from 0.01 to about 1.0 phr.

14. The method of claim 1, wherein the polyisoprene latex graphene composite composition is prepared by a process comprising steps of:
    (1) preparing a composition of at least partially reduced graphene oxide by:
        i. adjusting a pH of a graphene oxide composition to between about 8 and 12;
        ii. adding to the pH adjusted graphene oxide composition at least one curing agent selected from the group consisting of: sulfur, dithiocarbamate, a thiuram, thiourea, a thiazole, a guanidine, a metal oxide, and a mixture thereof; and
        iii. mixing the composition from step ii by agitation at a temperature in a range of from about 20° C. to about 80° C. for a time period in a range of about 4 to about 24 hours;
    (2) preparing a stabilized polyisoprene latex composition by mixing a polyisoprene latex with the at least one stabilizer under agitation for a time period in a range of about 4 to about 24 hours; and
    (3) combining the at least partially reduced graphene oxide composition of step (1) with the stabilized polyisoprene latex composition prepared in step (2) and mixing.

15. The method of claim 14, wherein the at least one curing agent comprises sulfur, dithiocarbamate, thiazole, zinc oxide or a mixture thereof.

16. The method of claim 15, wherein the dithiocarbamate is selected from the group consisting of zinc diethyldithiocarbamate, zinc dibutyldithiocarbamate, and a combination thereof, and wherein the thiazole is zinc 2-mercaptobenzothiazole.

17. The method of claim 14, wherein the at least one curing agent is in an amount of from 0.5 to 8.0 phr.

18. An elastomeric article prepared by the method according of claim 1.

19. The elastomeric article according to claim 18, wherein the elastomeric article is a condom, a glove, a probe cover or a catheter.

* * * * *